US00PP37069P2

(12) United States Plant Patent
Sidhu

(10) Patent No.: US PP37,069 P2
(45) Date of Patent: Oct. 28, 2025

(54) ***PAXISTIMA* PLANT NAMED 'Paxsid1'**

(50) Latin Name: *Paxistima myrsinites*
Varietal Denomination: Paxsid1

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 19/098,775

(22) Filed: Apr. 2, 2025

(30) Foreign Application Priority Data

Oct. 18, 2024 (CA) ..... PBR 24-11850

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Paxistima* plant named 'Paxsid1' that is characterized by its bushy, upright habit, its very good branching, and its foliage that is dark green in color.

3 Drawing Sheets

Botanical classification: *Paxistima myrsinites.*
Variety denomination: 'Paxsid1'.

BACKGROUND OF THE INVENTION

The present invention relates to a new and distinct cultivar of *Paxistima myrsinites* and will be referred to hereafter by its cultivar name, 'Paxsid1'. 'Paxsid1' is a new cultivar of Oregon boxwood grown for use as an ornamental landscape plant.

'Paxsid1' was discovered by the Inventor as a chance seedling in a trial garden planted with unnamed and unpatented plants of *Paxistima myrsinites* in Mission, British Columbia, Canada in summer of 2017. The exact parentage is unknown.

Asexual propagation of the new cultivar was first accomplished under the direction of the inventor by stem cuttings in October of 2017 in Mission, British Columbia, Canada. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Paxsid1' as a unique cultivar of *Paxistima.*

1. 'Paxsid1' exhibits a bushy, upright habit.
2. 'Paxsid1' exhibits very good branching.
3. 'Paxsid1' exhibits foliage that is dark green in color.

The plants of *Paxistima myrsinites* that were growing in the area of discovery had plants that were poorly branched and lacked a bushy plant habit. There are no known cultivars of *Paxistima myrsinites* known to the Inventor.

BRIEF DESCRIPTION OF THE DRAWINGS

The accompanying color photographs illustrate the overall appearance and distinct characteristics of the new *Paxistima.* The photographs were taken of 3-year-old plants as grown in a 2-gallon containers outdoors in a trial plot in St. Thomas, Ontario, Canada.

The photograph in FIG. 1 provides a side view of the plant habit of 'Paxsid1'.

Figure 1:
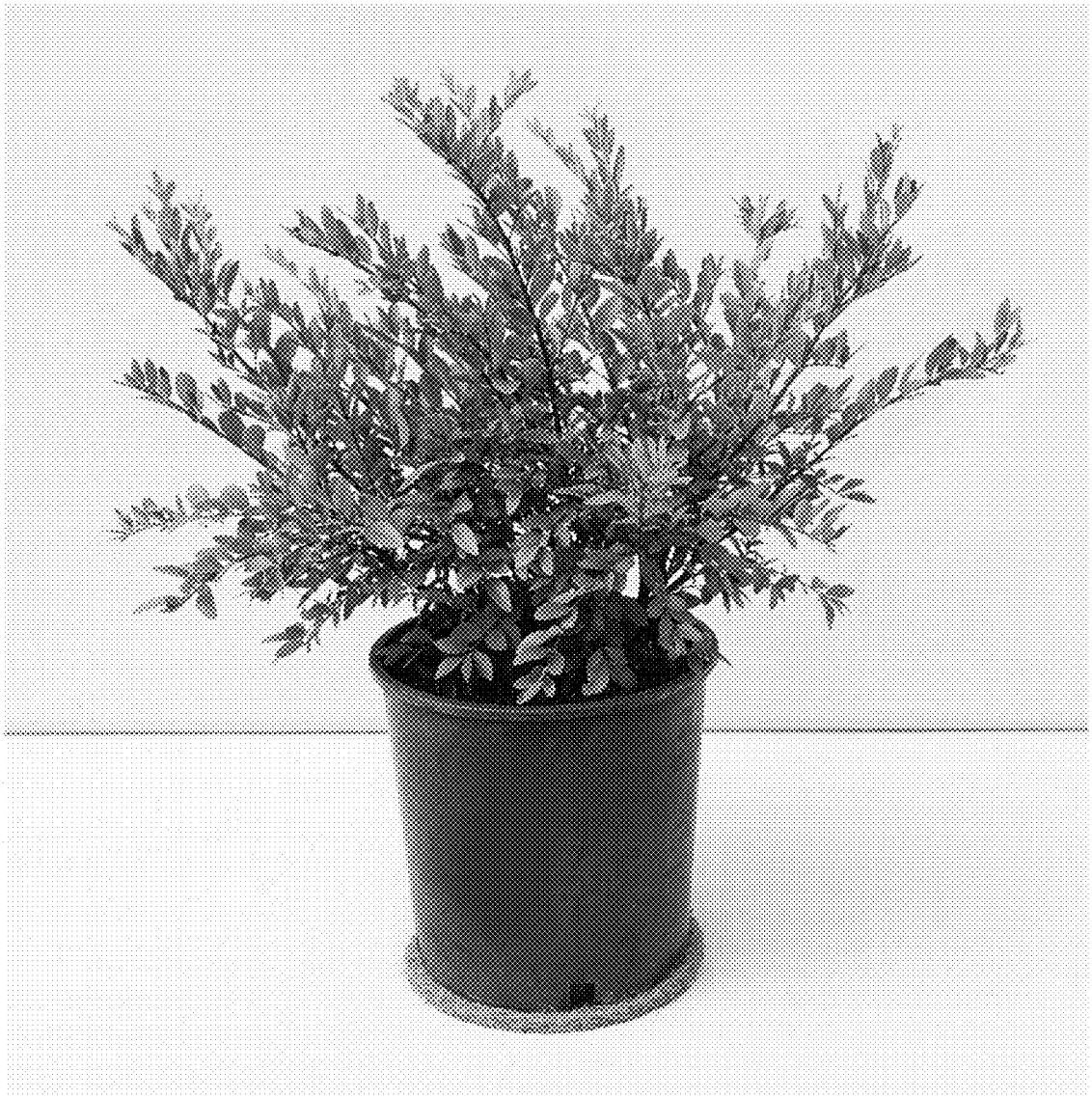
Figure 2:
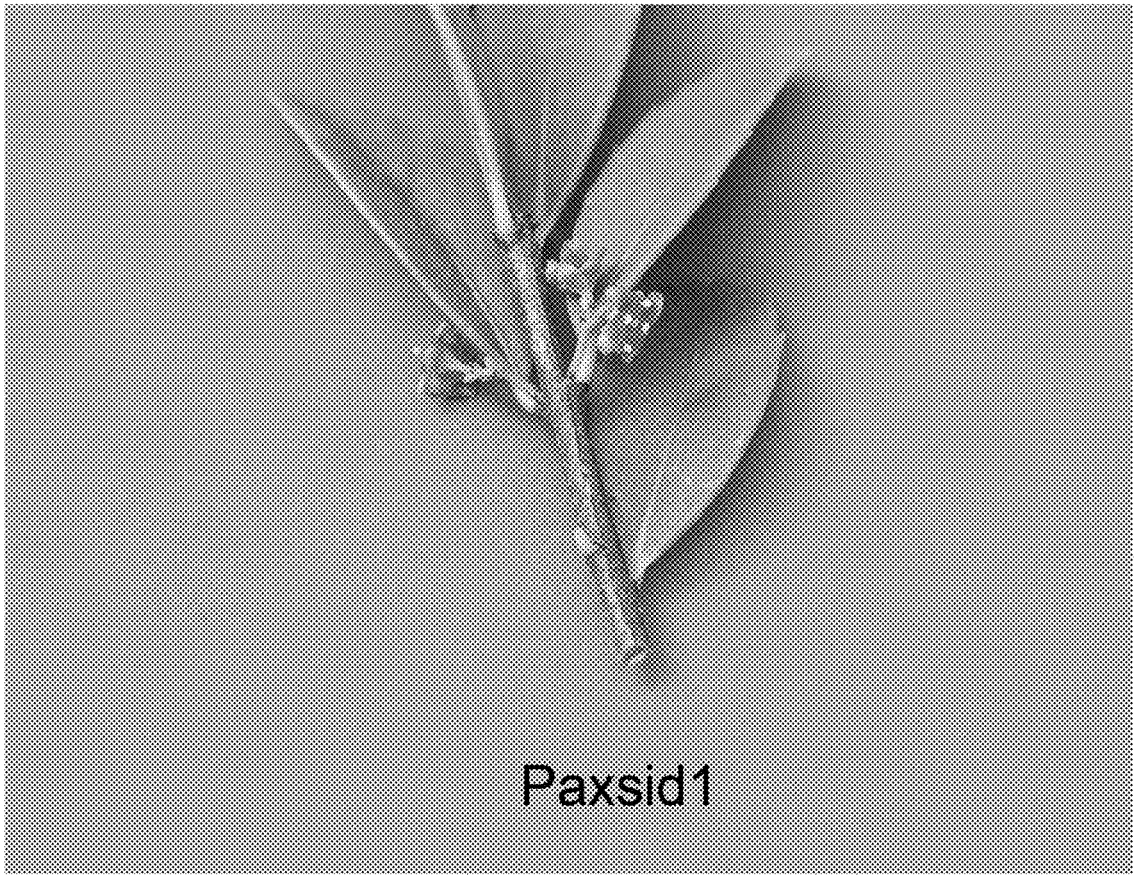

The photograph in FIG. 2 provides a close-up view of a blooming stem of 'Paxsid1'.

Figure 3:
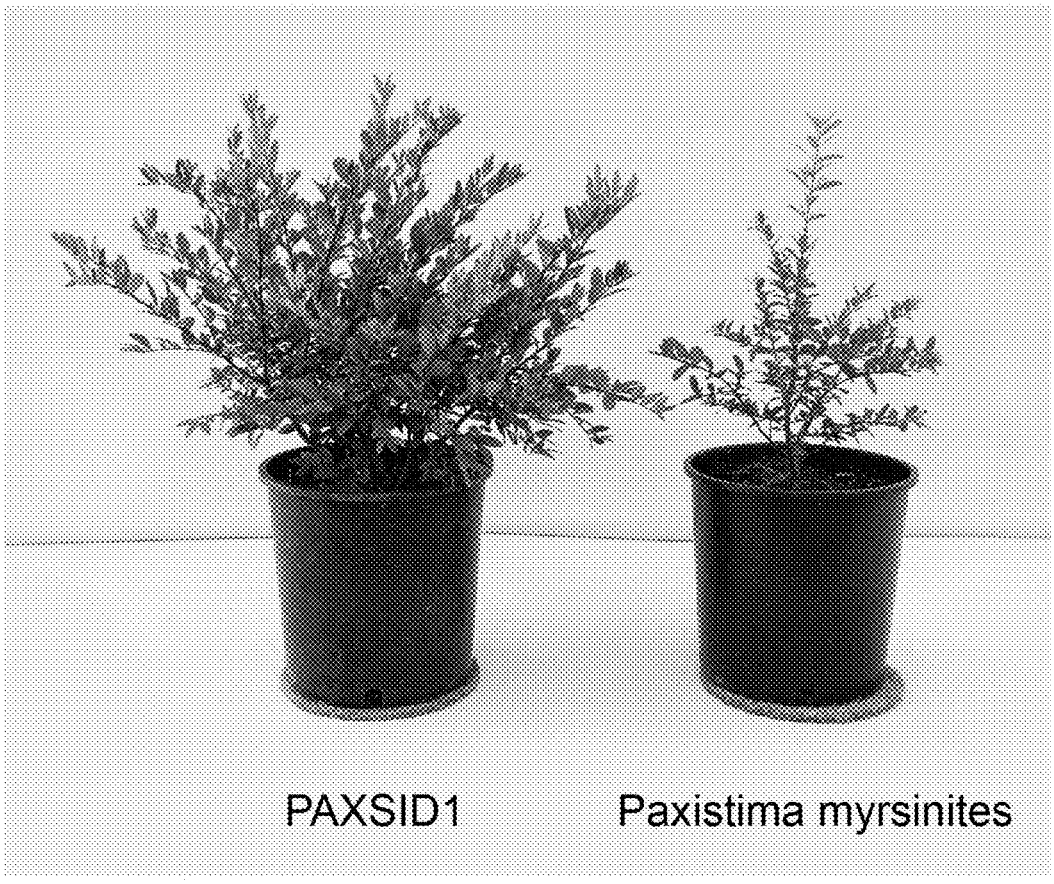

The photograph in FIG. 3 provides a side view of 'Paxsid1' and a typical plant of *Paxistima myrsinites.*

The colors in the photographs are as close as possible with the photographic and printing technology utilized and the color values cited in the detailed botanical description accurately describe the colors of the new *Paxistima.*

DETAILED BOTANICAL DESCRIPTION

The following is a detailed description of 3-year-old plants as grown in a 2-gallon container outdoors in a trial plot in St. Thomas, Ontario, Canada. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—June to July in Ontario, Canada.
*Plant type.*—Evergreen shrub.
*Plant habit.*—Upright, bushy.
*Height and spread.*—Reaches an average of 39 cm in height and 43 cm in width as a 3-year-old plant grown in a container.
*Hardiness.*—At least in USDA Zones 5 to 8.
*Diseases resistance.*—No susceptibility or resistance to diseases or pests has been observed.
*Root description.*—Fibrous.

*Propagation*.—Stem cuttings.

*Root development*.—A young rooted plant from a rooted cutting is produced in 12 weeks.

*Growth rate*.—Moderate.

Stem description:

*Stems*.—Densely branched, main; average of 4, lateral; 5, secondary lateral; 4 to 6.

*Stem size*.—Trunk; an average of 8.7 cm in length and 7.3 mm in diameter, main; an average of 3.9 cm in length, 4.7 mm in diameter, lateral; an average of 25.5 cm in length and 2.8 mm in diameter, secondary lateral; an average of 4.6 cm in length and 0.9 mm in diameter.

*Internode length*.—Average of 1.6 cm.

*Stem surface*.—Slightly glossy and smooth, older stems with slightly rugose, bark with numerous small lenticels ranging from 0.5 mm to 2 mm in length and 164C in color.

*Stem shape*.—Slightly edged.

*Stem aspect*.—Held in various angles between 45° and 75°.

*Stem strength*.—Strong.

*Stem color*.—Young and mature; 166A, older stems and trunk; N199B.

Foliage description:

*Leaf shape*.—Elliptic.

*Leaf division*.—Simple.

*Leaf base*.—Acute to obtuse.

*Leaf apex*.—Obtuse.

*Leaf venation*.—Pinnate; upper leaf midrib slightly raised, 146C in color, midrib less conspicuous on lower surface, 146C in color when visible.

*Leaf margins*.—Serrate incisions present on upper half of leaf.

*Leaf arrangement*.—Opposite, somewhat decussate along stem.

*Leaf aspect*.—Weakly concave.

*Leaf attachment*.—Petiolate.

*Leaf surface*.—Both surfaces are moderately glossy and smooth.

*Leaf size*.—Average of 3.2 cm in length and 1.5 cm in width.

*Leaf quantity*.—Average of 32 per lateral branch.

*Leaf color*.—Young leaves upper surface 144A to 144B, young leaves lower surface 145B, mature upper surface 146A, mature lower surface 146C.

Inflorescence description:

*Inflorescence*.—Flowers on axillary pedicels, located at the leaf axis, inconspicuous.

*Flower quantity*.—Solitary, in pairs, occasionally 3 flowers per peduncle.

*Flower form*.—Rotate.

*Flower size*.—An average of 3 mm in diameter and 2 mm in height.

*Petals*.—An average of 4, broadly ovate in shape, an average of 1 mm in length and 1.2 mm in width, obtuse apex, rounded base, entire margin, color upper and lower surface 47D, smooth and glabrous on upper and lower surfaces.

*Sepals*.—4, an average of 1 mm in length and width, broadly acute apex, entire margin, color upper and lower surfaces 144C, both surfaces glabrous.

*Calyx*.—An average of 2.0 mm in length and width, comprised of 4 fused sepals.

*Peduncles*.—An average of 3 mm in length, 145B to 145C in color, strong, smooth and glabrous surfaces.

*Pedicels*.—An average of 1.5 mm in length, 145B to 145C in color, strong, smooth and glabrous surfaces.

Reproductive organs:

*Gynoecium*.—1 pistil, stigma; 0.4 mm in length, 0.2 mm in width, 157B in color, ovary; 144B in color.

*Androecium*.—4 stamens, anthers; oblong in shape, approximately 0.2 mm in length and width, 10C in color, filaments; an average of 0.4 mm in length and 157B in color.

*Fruit and seed*.—None observed to date.

It is claimed:

1. A new and distinct cultivar of *Paxistima* plant named 'Paxsid1' as herein illustrated and described.

* * * * *